United States Patent
McKay (10) Patent No.: US 8,002,775 B2
(45) Date of Patent: Aug. 23, 2011

(54) METHODS AND INSTRUMENTS FOR TREATING PSEUDOARTHROSIS

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1151 days.

(21) Appl. No.: 10/399,836

(22) PCT Filed: Oct. 24, 2001

(86) PCT No.: PCT/US01/45479
§ 371 (c)(1),
(2), (4) Date: Oct. 24, 2003

(87) PCT Pub. No.: WO02/34113
PCT Pub. Date: May 2, 2002

(65) Prior Publication Data
US 2004/0064058 A1    Apr. 1, 2004

Related U.S. Application Data

(60) Provisional application No. 60/242,950, filed on Oct. 24, 2000.

(51) Int. Cl.
*A61B 17/00* (2006.01)
*A61M 5/178* (2006.01)

(52) U.S. Cl. .................................... 606/80; 604/164.01

(58) Field of Classification Search .................. 623/1.11, 623/1.12, 1.15–1.17, 1.21, 1.39, 1.4, 1.42–1.46; 604/103.01, 103.02, 500, 506–510, 164.01; 606/1.11, 1.12, 1.15–1.17, 1.21, 1.39, 1.4, 606/1.42–1.46, 80
See application file for complete search history.

(56) References Cited

U.S. PATENT DOCUMENTS

| | | | |
|---|---|---|---|
| 3,964,480 A | 6/1976 | Froning | |
| 4,013,080 A | 3/1977 | Froning | |
| 4,014,333 A | 3/1977 | McIntyre | |
| 4,808,158 A * | 2/1989 | Kreuzer et al. | 604/500 |
| 4,838,282 A * | 6/1989 | Strasser et al. | 600/567 |
| 5,012,818 A * | 5/1991 | Joishy | 600/567 |
| 5,190,548 A * | 3/1993 | Davis | 606/80 |
| 5,415,182 A | 5/1995 | Chin et al. | |
| 5,505,710 A * | 4/1996 | Dorsey, III | 604/158 |
| 5,575,650 A * | 11/1996 | Niznick et al. | 433/165 |
| 5,824,087 A * | 10/1998 | Aspden et al. | 606/94 |
| 5,968,008 A | 10/1999 | Grams | |
| 5,968,048 A * | 10/1999 | Harder | 606/80 |
| 6,007,570 A | 12/1999 | Sharkey et al. | |
| 6,126,682 A | 10/2000 | Sharkey et al. | |

(Continued)

FOREIGN PATENT DOCUMENTS
WO    WO 01/87195    11/2001

(Continued)

*Primary Examiner* — Theodore J Stigell
*Assistant Examiner* — Bradley J Osinski (57) ABSTRACT

Methods, instruments, and kits for treating spinal pseudoarthrosis are provided. In one embodiment, a method includes delivering to a location of spinal pseudoarthrosis an effective amount of an osteoinductive composition that includes an injectible osteoinductive composition that includes an injectible osteoinductive composition in a pharmaceutically acceptable carrier. In other embodiments, cannulated drills 10, 10', 10" and surgical instrument assemblies, 50, 50' including a drill and a syringe 60 and 60' wherein the syringe has a distal end that is matingly engaged to a proximal end of the drill are provided. The drill and other instruments, instrument assemblies, and kits formed therefrom may advantageously be used in a method for treating pseudoarthrosis.

30 Claims, 11 Drawing Sheets

U.S. PATENT DOCUMENTS

| | | |
|---|---|---|
| 6,241,710 B1 | 6/2001 | VanTassel et al. |
| 6,261,311 B1 | 7/2001 | Sharkey et al. |
| 6,300,127 B1 | 10/2001 | Hair et al. |
| 6,432,092 B2 | 8/2002 | Miller |
| 6,436,143 B1 | 8/2002 | Ross et al. |
| 6,517,568 B1 | 2/2003 | Sharkey et al. |
| 2001/0023349 A1 | 9/2001 | VanTassel et al. |
| 2002/0045942 A1 | 4/2002 | Ham |
| 2003/0014047 A1 | 1/2003 | Woloszko et al. |

FOREIGN PATENT DOCUMENTS

| | | |
|---|---|---|
| WO | WO 01/95818 | 12/2001 |
| WO | WO 02/34113 | 5/2002 |
| WO | WO 02/40070 | 5/2002 |

* cited by examiner

Fig. 19

METHODS AND INSTRUMENTS FOR TREATING PSEUDOARTHROSIS

CROSS-REFERENCE TO RELATED APPLICATION

The present application claims the benefit of U.S. Provisional Application Ser. No. 60/242,950 filed on Oct. 24, 2000, which is hereby incorporated by reference in its entirety.

BACKGROUND OF THE INVENTION

The present invention relates generally to methods and instruments for treating pseudoarthrosis.

Back pain affects millions of individuals and is a common cause of disability for the middle-aged working population. A frequent cause of back pain is rupture or degeneration of intervertebral discs. In many instances, the only relief from the symptoms of these conditions is a discectomy, or surgical removal of all or a portion of an intervertebral disc. Additionally, the disc space height must be maintained or restored.

One solution to the stabilization of an excised disc space is to fuse the adjacent vertebrae between their respective endplates. Typically a spacer or implant is inserted into the treated or prepared disc space until complete arthrodesis is achieved. The spacer/implant must provide temporary support and allow bone ingrowth. Success of the discectomy and fusion procedure requires development of a contiguous growth of bone or an osseous bridge to create a solid mass between the vertebrae to withstand the compressive loads on the spine for the life of the patient.

Several metal spacers have been developed to fill the void formed by the discectomy and to promote fusion. Sofamor Danek Group, Inc., (Memphis, Tenn.) markets a number of hollow spinal cages, and a wide variety of other such cages are known in the art. For example, U.S. Pat. Nos. 5,015,247 and 5,984,967 to Michelson et al. and Zdeblick et al., respectively, disclose threaded spinal cages. The cages are hollow and can be filled with osteoinductive material, such as autograft and allograft, prior to insertion into the intervertebral disc space. Apertures defined in the cages communicate with the hollow interior to provide a path for tissue growth between the vertebral endplates.

Although some success with respect to spinal fusions has generally been obtained with respect to interbody fusions or intertransverse process fusions, the incidence of pseudoarthrosis, also known as pseudarthrosis, or failure of a spinal fusion, may be relatively high in certain circumstances. For example, the incidence of pseudoarthrosis has been reported as high as 40% for smokers, as well as for patients having multilevel fusions and unrecognized metabolic disease. Pseudoarthrosis has been shown to be the contributing cause of symptoms in 78% of symptomatic patients requiring reoperation, with each reparative procedure decreasing the probability of success. Moreover, at least about 90% of attempted posterolateral intertransverse process fusions with autogenous iliac crest bone grafting in Lewis rats fail.

In order to treat symptomatic pseudoarthrosis, a conventional, open surgical procedure includes direct exposure of the fusion mass, decortication, bone regrading and possibly reinstrumentation or addition of new graft and/or new instrumentation. The repair procedure can be very complex, is highly invasive and additional posterior fusion procedures may need to be performed to stabilize the spine after a fusion has failed. Thus, simpler, less invasive methods for treating spinal pseudoarthrosis are needed.

SUMMARY OF THE INVENTION

It has been discovered that administration of an osteoinductive composition to a location of pseudoarthrosis, such as spinal pseudoarthrosis, is effective in promoting bone growth for treating the pseudoarthrosis. Accordingly, in one aspect of the invention, methods of treating spinal pseudoarthrosis are provided.

In one form of the invention, a method includes delivering to a location of pseudoarthrosis an effective amount of an osteoinductive composition. Preferably the osteoinductive composition is combined with an acceptable carrier, such as a calcium phosphate-containing carrier. The osteoinductive composition is effective in promoting bone growth for treating the spinal pseudoarthrosis.

In preferred forms, the method includes advancing a first elongated member to a location of spinal pseudoarthrosis in a patient. The first elongated member has a proximal end, a distal end and a lumen extending longitudinally therethrough. The method further includes advancing the osteoinductive composition described herein through the lumen of the first elongated member. In other preferred forms of the invention, the osteoinductive composition is advanced through the lumen of the elongated member to a pseudoarthrotic mass into and extending across the pesudoarthrotic mass.

The methods described herein may be accomplished with or without decortication and, in the case of a failed interbody fusion, without removal of the implant. Further the methods can use minimally invasive surgical procedures that can significantly reduce morbidity associated with surgery, reduce the duration of a hospital stay and reduce patient recovery times.

In other aspects of the invention, surgical instruments are provided. The instruments are advantageously configured for use in the methods of treating spinal pseudoarthrosis described herein. In one form of the invention, a cannulated drill is provided that includes an elongated member having a proximal end, a distal end, an inner surface, and an outer surface. The inner surface defines a lumen that extends along the length of the elongated member and is sized to receive an elongated obturator. The distal end of the elongated member has at least one bone cutting edge. The proximal end of the elongated member has a connector configured for matingly engaging a distal end of a syringe to the proximal end of the elongated member. The elongated member is preferably formed of a biocompatible material.

Surgical instrument assemblies are also provided including at least the cannulated drill described herein and a syringe. The syringe has a housing that defines a cavity and has a proximal end and a distal end. The distal end of the syringe is matingly engageable to the proximal end of the elongated member. The lumen of the elongated member and the cavity of the housing are in fluid communication when the distal end of the syringe and the proximal end of the elongated member are matingly engaged.

DESCRIPTION OF THE EMBODIMENTS

For the purposes of promoting an understanding of the principles of the invention, reference will now be made to embodiments and specific language will be used to describe the same. It will nevertheless be understood that no limitation of the scope of the invention is thereby intended, such alterations and further modifications of the invention and such further applications of the principles of the invention as illustrated herein, being contemplated as would normally occur to one skilled in the art to which the invention relates.

The present invention relates to methods and instruments for treating pseudoarthrosis. Pseudoarthrosis, also known as pseudarthrosis, refers to a condition that arises due to an incomplete bone fusion process. With respect to spinal pseudoarthrosis, this includes failure of adjacent vertebrae to fuse or the presence of some other bone discontinuity in the fusion mass. That is, the bone of the spinal fusion is not contiguous, such that a non-union, or a gap between the bone, exists. In a first aspect of the invention, embodiments of methods include delivering to a location of spinal pseudoarthrosis an effective amount of an osteoinductive composition. The composition advantageously includes an osteoinductive factor, such as in a pharmaceutically acceptable carrier. The osteoinductive composition is effective in promoting bone growth to treat the spinal pseudoarthrosis.

In a second aspect of the invention, embodiments of surgical instruments are provided. In one form, a surgical instrument includes a cannulated drill including an elongated member formed of a biocompatible material and having a proximal end, a distal end, an inner surface, and an outer surface. The inner surface defines a lumen that extends along the length of the elongated member and is sized to receive an elongated obturator. The distal end of the elongated member has at least one bone cutting edge. The proximal end of the elongated member has, or otherwise defines, a connector configured to matingly engage a distal end of a syringe. Embodiments of surgical instrument assemblies are also provided that include the drill described herein and a syringe. In addition or in the alternative, the surgical assemblies can include a cannulated drill and obturator for sliding engagement within an interior region of the cannulated drill. One or more of the surgical assemblies can be provided for delivery of a flowable or injectable osteoinductive composition into a desired treatment site. Embodiments of kits for treating pseudoarthrosis that include a combination of the surgical instruments and/or instrument assemblies described herein are also provided.

Figure 1:
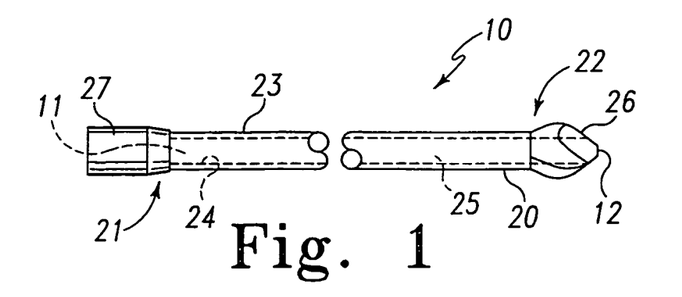
FIG. 1 is a side elevation view of one embodiment of a drill provided according to the present invention.
Figure 2:
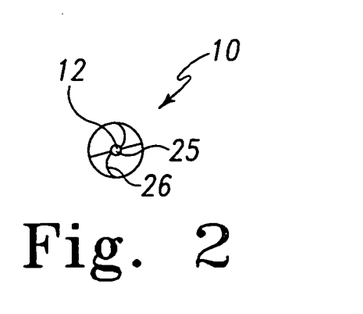
FIG. 2 is a first end view of the drill of FIG. 1.

As disclosed above, in one aspect of the invention, surgical instruments may be advantageously utilized in a procedure for treating pseudoarthorosis. Embodiments of these instruments will be described first in order to facilitate the discussion herein of the methods of treating spinal pseudoarthrosis. In one embodiment, a surgical instrument includes an elongated channel-forming and delivery member such as a drill 10 as seen in FIGS. 1 and 2. Drill 10 comprises an elongated member 20 having a proximal end 21, a distal end 22, an exterior surface 23 and an inner surface 24. Distal end 22 has at least one bone cutting edge 26, and preferably about two to about four cutting edges for cutting bone. Alternately, the drill may include any device capable of forming a passageway or channel in or adjacent to the site of pseudoarthrosis, such as a piercing device, milling device, etc.

Inner surface 24 defines a lumen 25 extending along the length of elongated member 20, typically from proximal end 21 to distal end 22. Lumen 25 is illustrated as a cylindrical channel having a first opening 11 adjacent to proximal end 21, and a second opening 12 proximate to distal end 22 permitting access through the interior of drill 10. Moreover, lumen 25 of elongated member 20 is sized to receive an obturator (not shown). In another embodiment, lumen 25 is sized to receive a guide wire, such as, a K-wire. The guide wire can be selected to be any desired diameter and/or length. The guide wire can be inserted into a treatment site to facilitate desired placement of drill 10 during treatment.

Proximal end 21 of elongated member 20 is advantageously configured for mating with a syringe. Proximal end 21 of elongated member 20 may therefore include, or otherwise define, a connector 27 that matingly engages the distal end of a syringe to proximal end 21 of elongated member 20. The connector may be formed integral with the elongated member or may be separately connected thereto, such as by use of press-fit threaded connectors, adhesives and any other securing methods or combinations thereof. A wide variety of connectors may be utilized, including luer-lock connectors, Moorse taper connectors and snap-lock connectors.

Figure 3:
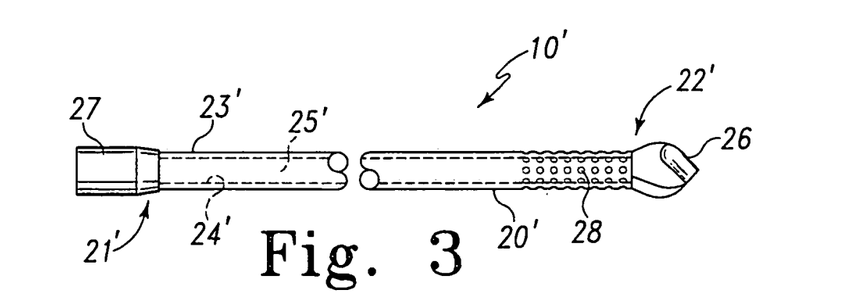
FIG. 3 is a side elevation of an alternative embodiment of a drill having a plurality of apertures extending along a length of the drill for use in the present invention.

FIG. 3 illustrates an alternative embodiment of a drill 10' for use in the present invention. Drill 10' is formed similar to drill 10 and like reference numbers with a prime are used to denote like elements. Drill 10' includes a plurality of apertures 28 extending through exterior surface 23' to inner surface 24'. Preferably, apertures 28 are provided in a desired size, number and location along a length of the drill 10'. In one embodiment, the apertures are sized and located to effectively deposit an osteoinductive material across a pseudoarthrotic region of the spine with minimal or no repositioning of the drill. In the illustrated embodiment a plurality of apertures 28 are located proximate to distal end 22'.

Figure 4:
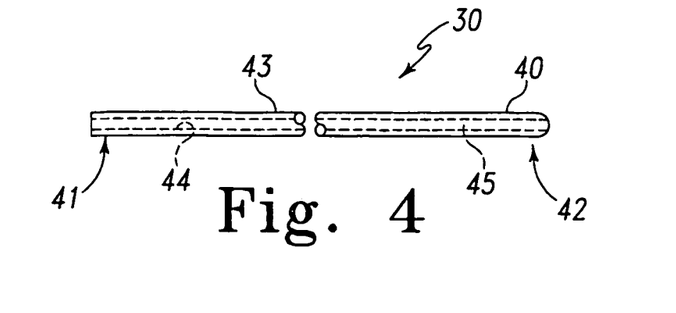
FIG. 4 is a side elevation view of an elongated obturator for use in a drill according to the present invention.
Figure 5:
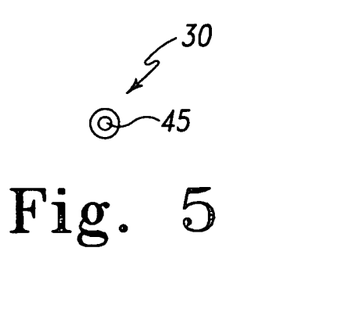
FIG. 5 is a first end view of the obturator of FIG. 4.
Figure 6A:
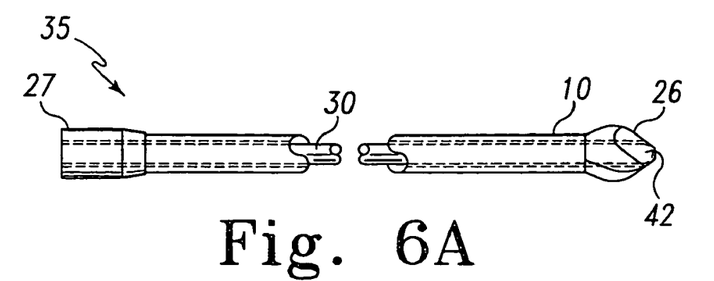
FIG. 6A is a side elevation view partially broken away of an obturator/drill assembly according to the present invention.
Figure 6B:
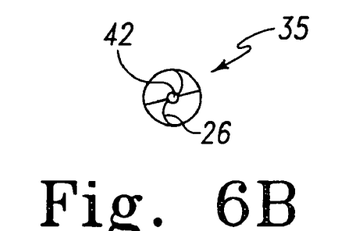
FIG. 6B is a first end view of the obturator/drill assembly of FIG. 6.

Referring now to FIGS. 4 and 5, one embodiment of a lumen-blocking device such as obturator 30 comprises an elongated member 40 having a proximal end 41, a distal end 42, an outer surface 43 and an inner surface 44. Inner surface 44 defines a lumen 45 that extends along the length of elongated member 40, typically from proximal end 41 to distal end 42. Obturator 30 may be advantageously designed and configured to conform to inner surface 24 of elongated member 20 of drills 10 and/or 10' and/or be slidably received within lumen 25 and/or 25'. Although obturator 30 may be variously shaped, in one form of the invention obturator 30 is cylindrical. For example, obturator 30 is slidably disposed in lumen 20 of drill 10 to provide assembly 35 as best seen in FIG. 6A and FIG. 6B. Obturator 30 can be sized and configured to inhibit material from entering the lumen of the drill during the drilling process.

Figure 7:
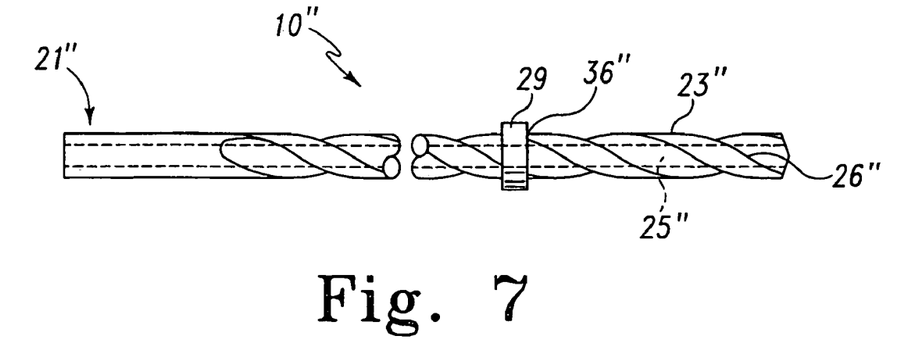
FIG. 7 is a side elevation view of an alternative embodiment of a drill for use in the present invention.

In other forms of the invention, yet other drills may be utilized. Referring to FIG. 7, a drill 10" is shown. Drill 10" is formed similar to drill 10 and like reference numbers with a double prime are used to denote like elements. Drill 10" advantageously may have a built-in depth gauge 29. Depth gauge 29 can be movably secured to a portion of surface 23" that limits the drilling depth of drill 10". Depth gauge 29 may be positionable during surgery. For example, the surgeon can determine a desired depth to bore into a bone or pseudoarthrotic site using x-ray, Computer Tomography (CT), fluoroscopy or other techniques. The surgeon can then measure a distance from distal end 26" toward proximal end 21'" equal to the desired bore depth. The surgeon can then position depth gauge 29 at a position 36 from the distal end of drill 10" equal to the desired bore depth. Depth gauge 29 can be secured in the desired position using a set screw, or other locking mechanism.

The drills and obturators described herein may be formed of biocompatible materials. In preferred forms of the invention, the drill and obturator may be formed from metallic materials, including stainless steel, titanium, and alloys thereof. Other suitable materials include nitinol, or other shape memory materials.

Figure 8A:
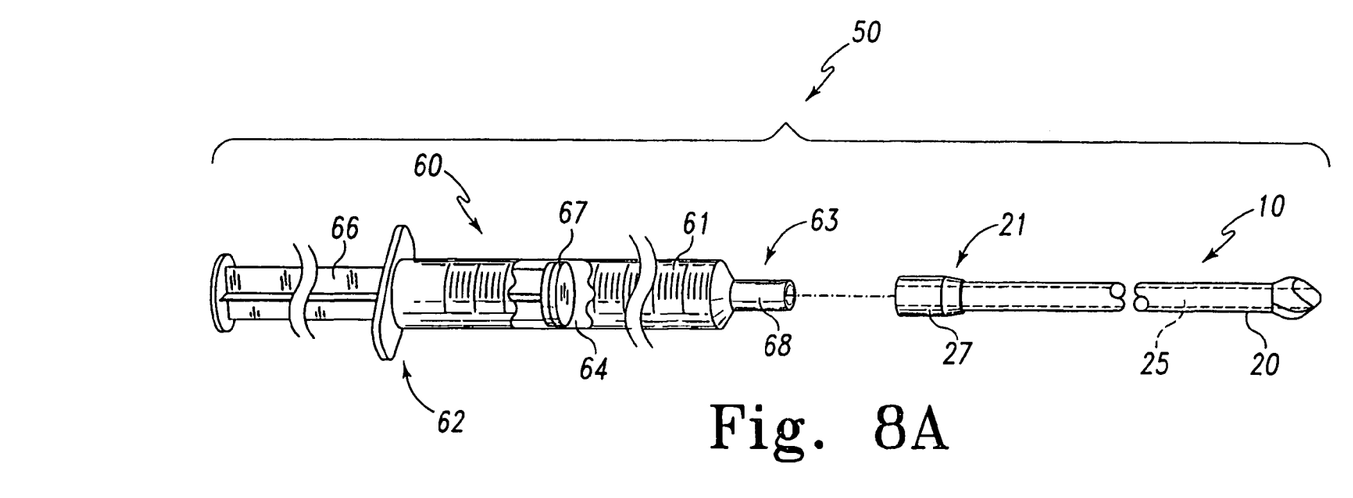
FIG. 8A is an exploded view of a syringe-drill assembly provided according to the present invention.

In another aspect of the invention, embodiments of surgical instrument assemblies are provided. Referring now to FIG. 8A, in one form of the invention, a surgical instrument assembly 50 includes drill 10 and syringe 60. While drill 10 is illustrated it is understood that any of drills 10, 10' and/or 10" can be included in the assembly. Syringe 60 may be any device capable of delivering an osteoinductive composition.

In one embodiment, syringe 60 includes a barrel, or housing, 61 having a proximal end 62 and a distal end 63. Housing 61 defines a cavity, or chamber, 64 for retaining a composition to be delivered. Plunger 66 having a plunger head 67 is disposed in cavity 64 of syringe 60. Distal end 63 defines a connector portion 68 such as a luer-lock connector provided to releasably engage connector 27 of drill 10.

Figure 8B:
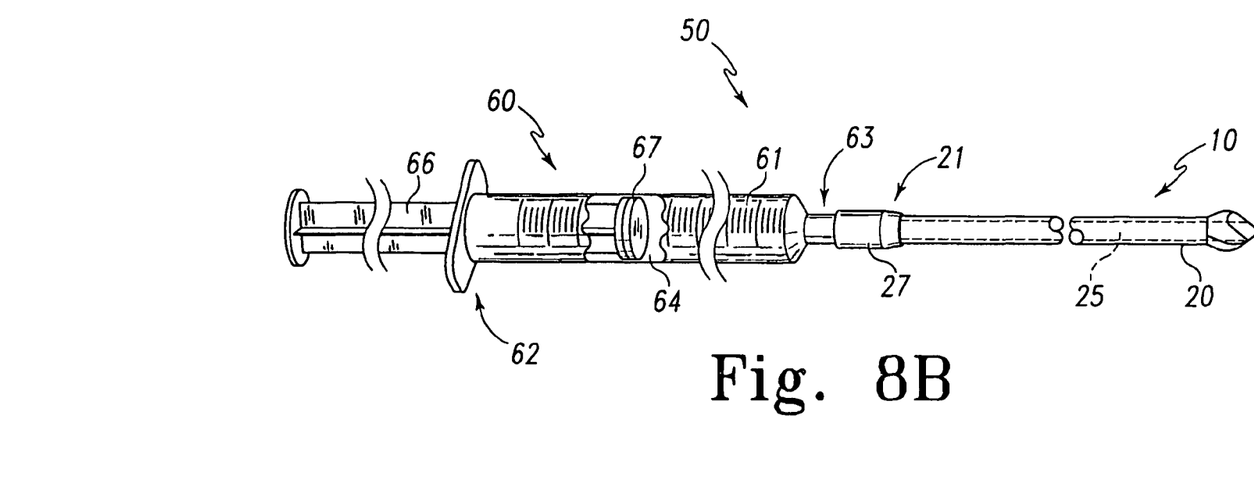
FIG. 8B is a side elevation view of the syringe-drill assembly of FIG. 8A.

Referring additionally to FIG. 8B, distal end 63 of syringe 60 is matingly engaged to proximal end 21 of drill 10. When so engaged, chamber 64 of syringe 60 is in fluid communication with lumen 25 of drill 10 to form surgical instrument assembly 50. Syringe 60 may be formed of a material that does not react with osteoinductive compositions, such as polymeric materials, including metal, glass, and synthetic polymers, such as polyalkenes, including polyethylene, polypropylene, poly(vinyl chloride), and polystryrene.

Figures 8C, 9:
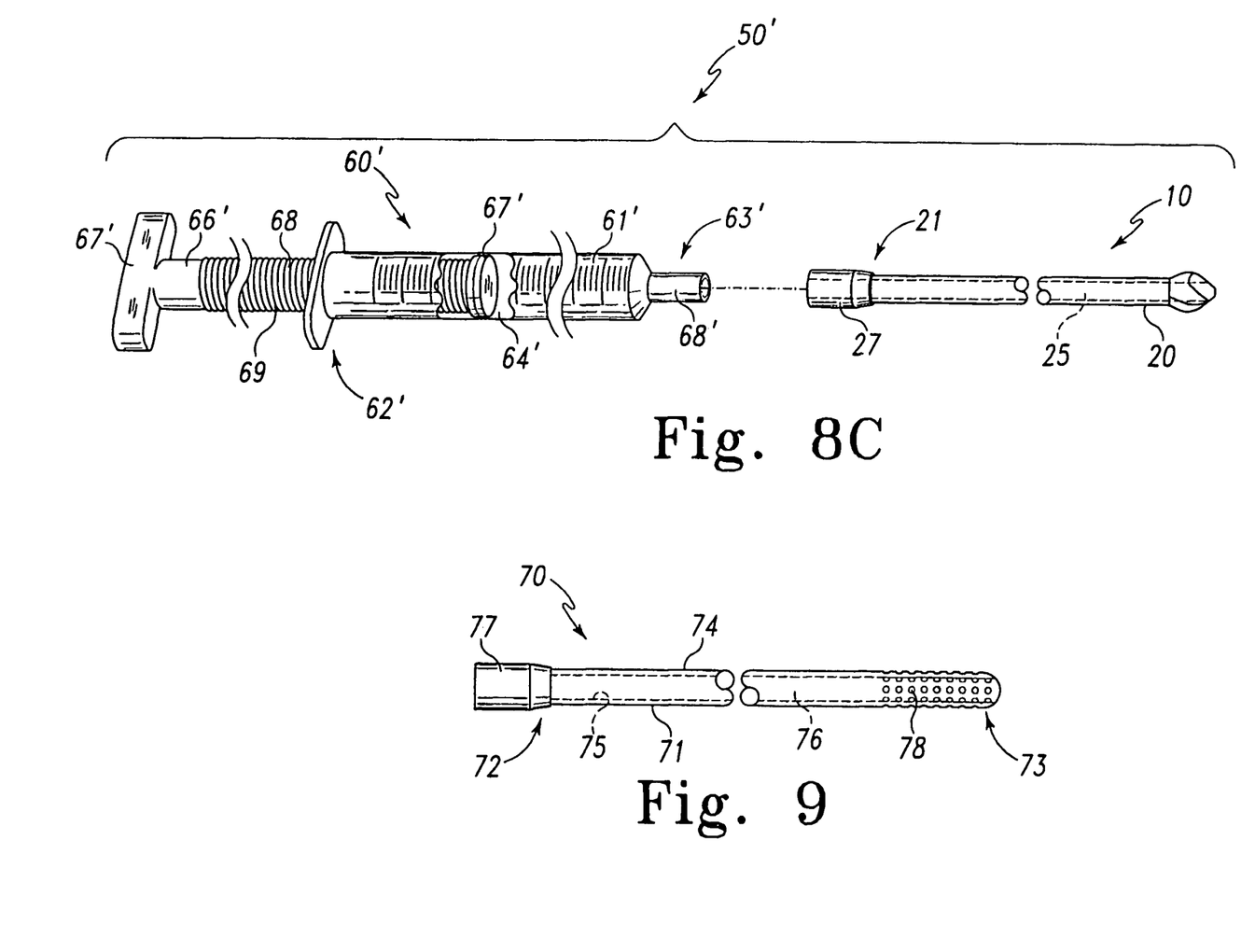
FIG. 8C is an exploded view of an alternative embodiment of a syringe-drill assembly provided according to the present invention.
FIG. 9 is a side elevation view an elongated delivery member having apertures extending along a length of the member provided according to the present invention.

Referring to FIG. 8C, an alternative surgical instrument assembly is shown that includes drill 10 and syringe 60'. As above noted while drill 10 is illustrated in assembly 50' any of drills 10, 10' and 10" can be combined with syringe 60'. Syringe 60' is formed similar to syringe 60, and thus like reference numbers denote similar components but are denoted with a prime. Plunger 66' includes one or more threads 68 extending along a length of plunger shaft 69. Threads 68 can facilitate incremental adjustment of plunger 66 in chamber 64, and, consequently, facilitate withdrawing or expulsion of material into or out of chamber 64.

As seen in FIG. 9, in another embodiment, an elongated delivery member 70 fluidly connectable with an osteoinductive material delivery device includes an elongated member 71 having a proximal end 72, a distal end 73, an outer surface 74 and an inner surface 75. Inner surface 75 defines a lumen 76 extending along the length of elongated member 71, typically from proximal end 72 to distal end 73. In one embodiment, distal end 73 can be closed. Alternatively, distal end 73 can include one or more openings extending therethrough providing communication with lumen 76. Furthermore, elongated member 71 may have a plurality of apertures, or other openings or perforations, 78 extending through outer surface 74 anywhere along a length of elongated member 71, such as adjacent to distal end 73. Proximal end 72 may have a connector 77 for matingly engaging a syringe and may be similar to the connectors 27 described above for the drill 10.

In another form, the invention provides methods for treating pseudoarthrosis. The methods may be minimally invasive. For example, an incision is typically made that is no greater than about 30 mm in length so as to substantially reduce exposure of internal body components. In such methods, a cannula is inserted into the body through which the necessary tools may be delivered to, and manipulated at, the surgical site. The methods are thus typically performed percutaneously. Although the methods may be used to treat a wide variety of pseudoarthroses, including long bone nonunions, they are advantageously used to treat spinal pseudoarthroses, especially spinal pseudoarthroses at an interbody fusion site, such as at the location of a damaged or diseased spinal disc, or a transverse process fusion site, such as an intertransverse process fusion site.

In one embodiment of the invention, a treatment method includes delivering to a desired location proximate to a spinal pseudoarthrosis an effective amount of an osteoinductive composition. The osteoinductive composition is advantageously injected, or otherwise placed, proximate to or directly into the pseudoarthrotic mass.

As defined herein, a pseudoarthrotic mass is a collection of tissue found at a location of pseudoarthrosis, including bone pieces, or fragments thereof, that have not completely united with each other to provide a desired bone mass or joined as desired to adjacent bone. The bone pieces and/or fragments can be interspersed, or otherwise dispersed, among fibrous tissue. Additionally or alternatively the bone mass can include undesired discontinuities. Additionally a pseudoarthrotic mass can include a unitary bone mass having undesirable cracks or voids extending thereon. That is, the bone may not be continuous from one end or side of the pseudoarthrotic mass to the other end or side as desired.

Channels, boreholes or other spaces, are created in the bone adjacent to the pseudoarthrotic mass. Drilling into the pseduoarthrosis will create some bleeding bone releasing osteogenic cells that can respond to the presence of bone morphogenic proteins (BMP). The BMP causes these osteogenic cells or stem cells to become osteoblast, which go on to form bone.

Additionally after the boreholes are formed, an osteoinductive composition can be injected into the channels may be on both sides of the non-union, as well as across the non-union, or bone discontinuity cracks and/or voids. That is, the osteoinductive composition, after injection, will extend from channels or other spaces created in the bone on one side of the fibrous tissue of the pseudoarthrotic mass, through the fibrous tissue of the mass and into the channels or other spaces created in the bone on an opposing, or other side of the fibrous tissue.

Although not being limited by theory, it is believed that the osteoinductive composition will be released into the fibrous tissue and bone mass resulting in new bone formation. The osteoinductive composition may then cause an initial osteoclastic resorption followed by a spurt of new bone formation in and/or adjacent to the area of injection. The osteoinductive composition can thus lead to ossification of soft tissue, such as scar or other tissue in a failed fusion. It is further believed that, once a solid connection is made across the pseudoarthrotic mass and thus allowing the bone at the site to be substantially continuous, the new bone and host bone will remodel due to the new loading environment and continue to become stronger, thus adapting to the new loads.

In performing the methods, the area of non-union in the pseudoarthrotic mass may be first located by Computer Tomography (CT). The non-union is seen as a radiolucent area representing fibrous tissue. In pseudoarthroses at interbody fusion sites, the radiolucent areas are frequently seen at the interface of the intervertebral spacer, or fusion cage, and the adjacent vertebral body.

In another aspect of the invention, kits for treating spinal pseudoarthrosis are provided. Embodiments of the kits may include one or more drills 10, 10', 10", syringes 60 and 60', obturator 30 and/or delivery number 70 as described herein. Preferably the drills 10, 10', 10", syringes 60, 60' and/or obturator 30 are provided to interengage with one another to form one or more surgical assemblies. In addition or in the alternative, the kits can include drills, syringes, obturator, guide wires for treatment that do not interengage with each other. Furthermore, the kits may include an obturator, a syringe, an elongated delivery member and a cannulated drill having a proximal end without connector.

Figure 10A:
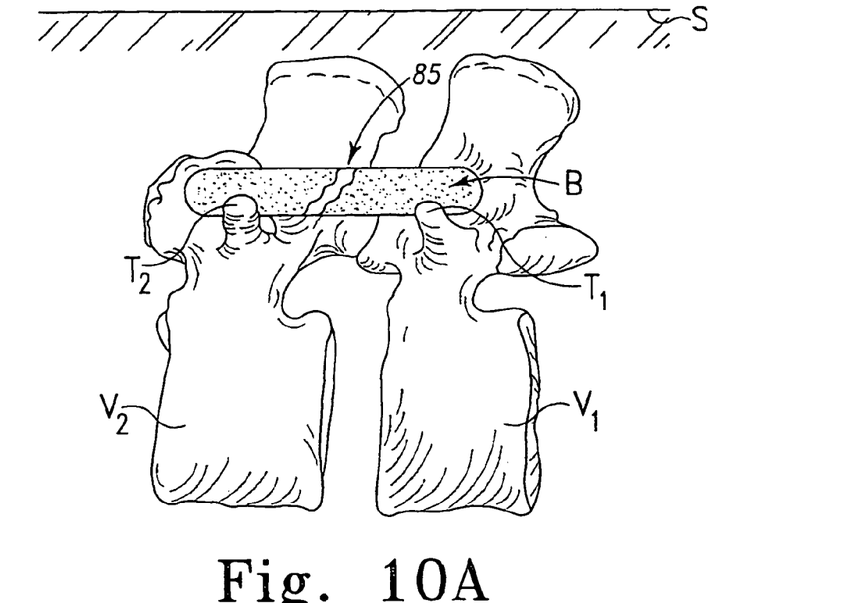
FIG. 10A is a side elevation view of a pair of vertebrae depicting pseudoarthrosis at an intertransverse process fusion site.
Figure 10B:
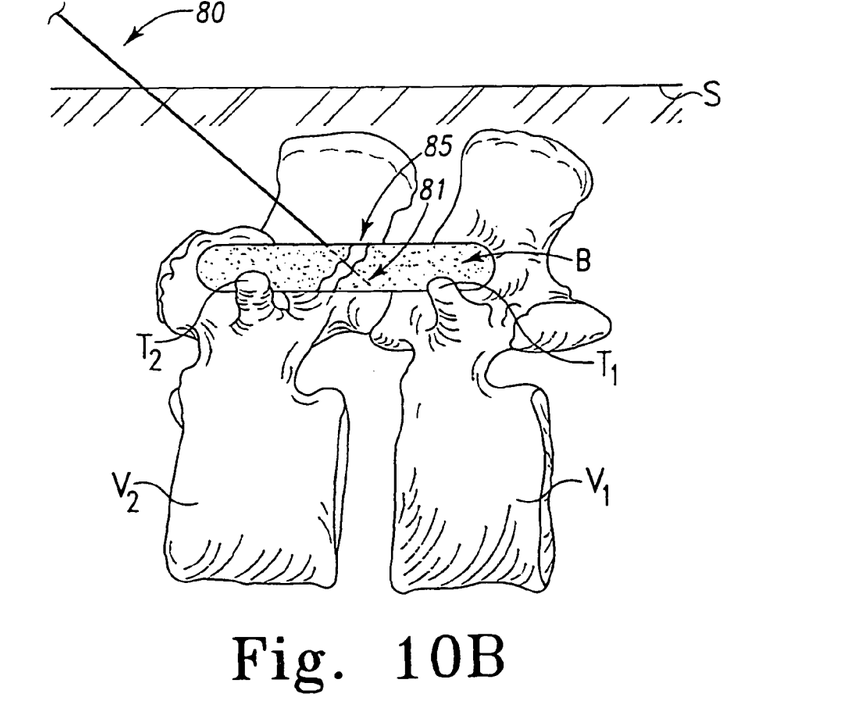
FIG. 10B is a side elevation view of the pseudoarthrosis of the pair of vertebrae of FIG. 10A with a guide wire inserted into a pseudoarthrotic mass.
Figure 11:
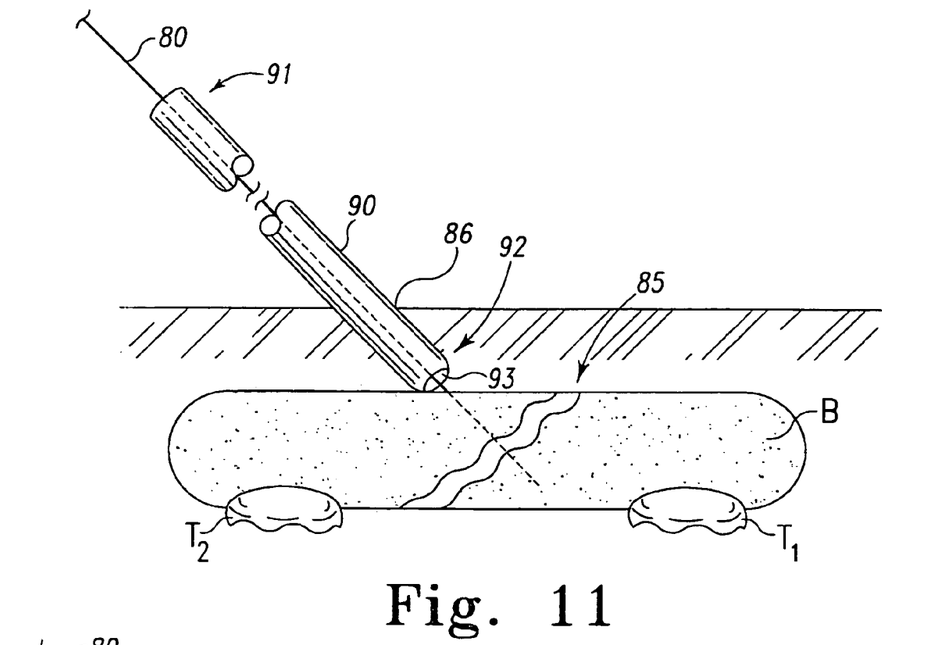
FIG. 11 is an enlarged view of the pseudoarthrosis site of FIG. 10A illustrating a cannula positioned adjacent the treatment site.

Referring now to FIGS. 10A and 10B, a pseudoarthrotic mass or defect 85 adjacent to bone tissue B is seen at a failed intertransverse process fusion site involving transverse process $T_1$ and $T_2$ of vertebra $V_1$ and $V_2$, respectively. In one embodiment of treating this spinal pseudoarthrosis, a K-wire 80, or other similar guide wire having a pointed or otherwise sharpened or piercing distal end 81, is inserted percutaneously through skin surface S and through bone adjacent to the area of non-union or pseudoarthrotic mass 85, through the non-union and into bone on the other side of the non-union under fluoroscopic guidance as seen in FIG. 10B. Thus, K-wire 80 extends from bone tissue on one side of the fibrous tissue of pseudoarthrotic mass 85, through a defect or fibrous tissue of the pseudoarthrotic mass and into bone on the other side of the defect or fibrous tissue. Placement of wire 80 can be monitored using CT, fluoroscopy or other techniques during surgery.

Referring now to FIGS. 11-14, an incision 86 is made in the outer tissue layers. Incision 86 allows ready placement and positioning of cannula 90. Incision 86 may be sufficient by small and minimally invasive to decrease disruption of adjacent tissue, minimize patient discomfort, and promote rapid patient recovery.

Figure 12:
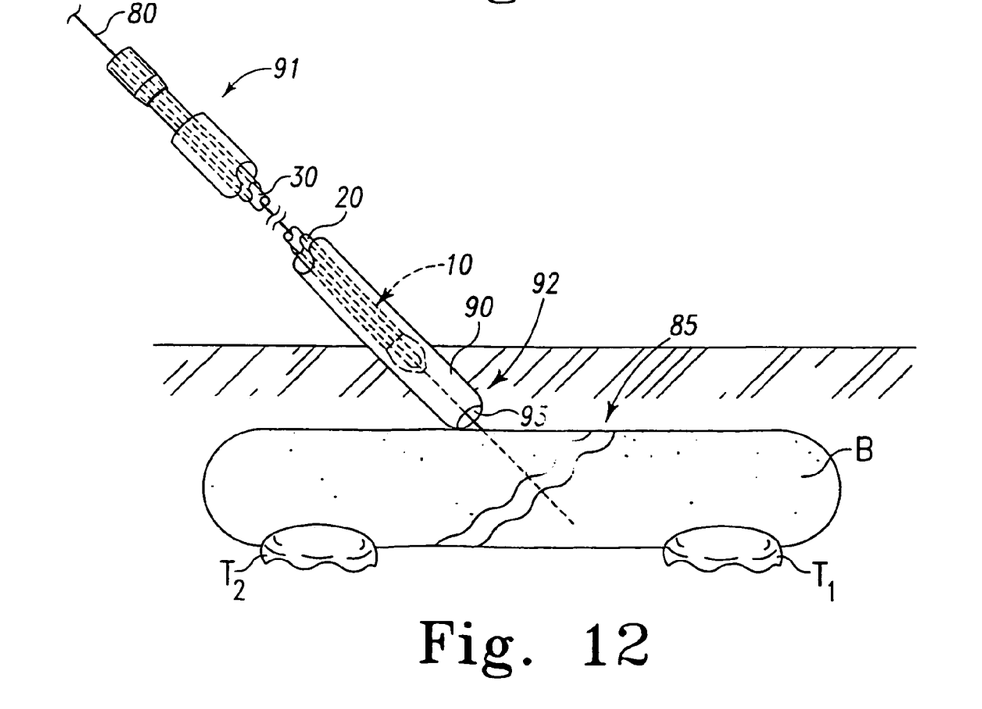
FIG. 12 is a side elevation view of the pseudoarthrotic mass of FIG. 11 depicting a cannulated drill having an obturator disposed in its lumen.

Distal end 92 of cannula 90 is advanced through incision 86 adjacent to the selected treatment site, along K-wire 80. Cannula may include a distal end that is rounded to facilitate insertion of the cannula and to reduce complications that may arise during its insertion, such as tissue injury. A cannulated drill such as drill 10 having disposed in its lumen obturator 30 is then advanced along K-wire 80 from proximal end 91 of cannula 90 and through lumen 93 of cannula 90 to the selected location for treatment of the spinal pseudoarthrosis and adjacent distal end 92 of cannula 90 as seen in FIG. 12.

Figure 13:
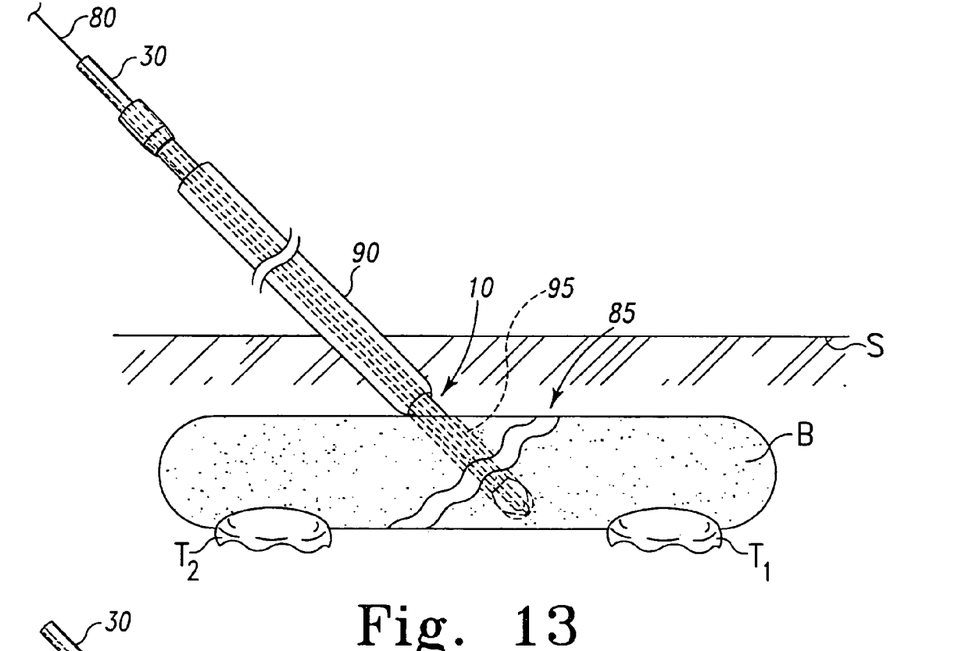
FIG. 13 is a side elevation view of FIG. 12 depicting a drill in a bored hole in the pseudoarthrotic mass.
Figure 14:
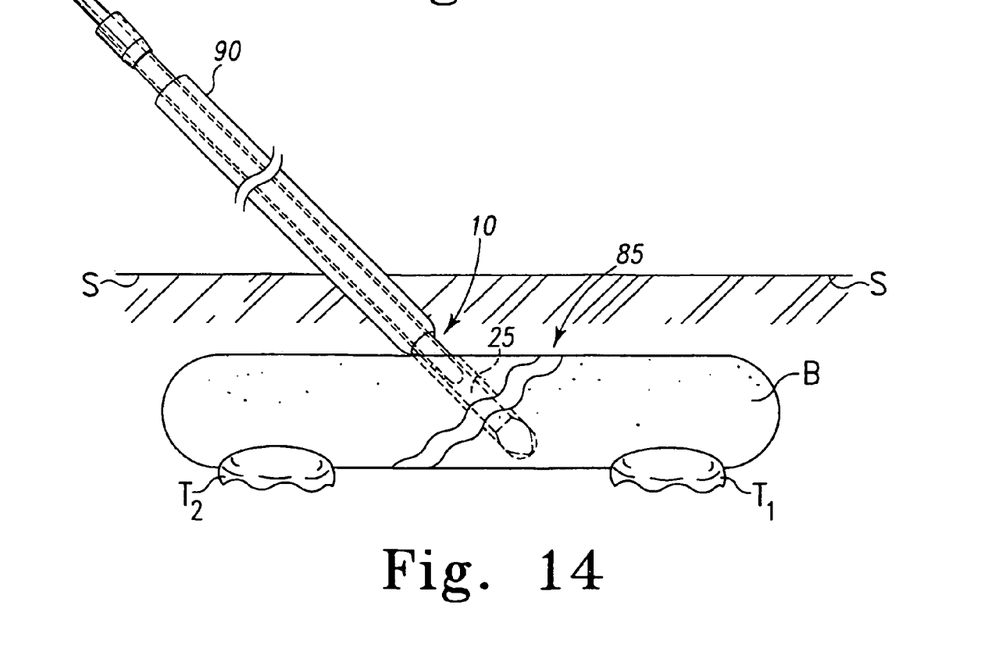
FIG. 14 is a side elevation view of the pseudoarthrotic mass of FIG. 13 depicting the drill without the obturator.
Figure 15:
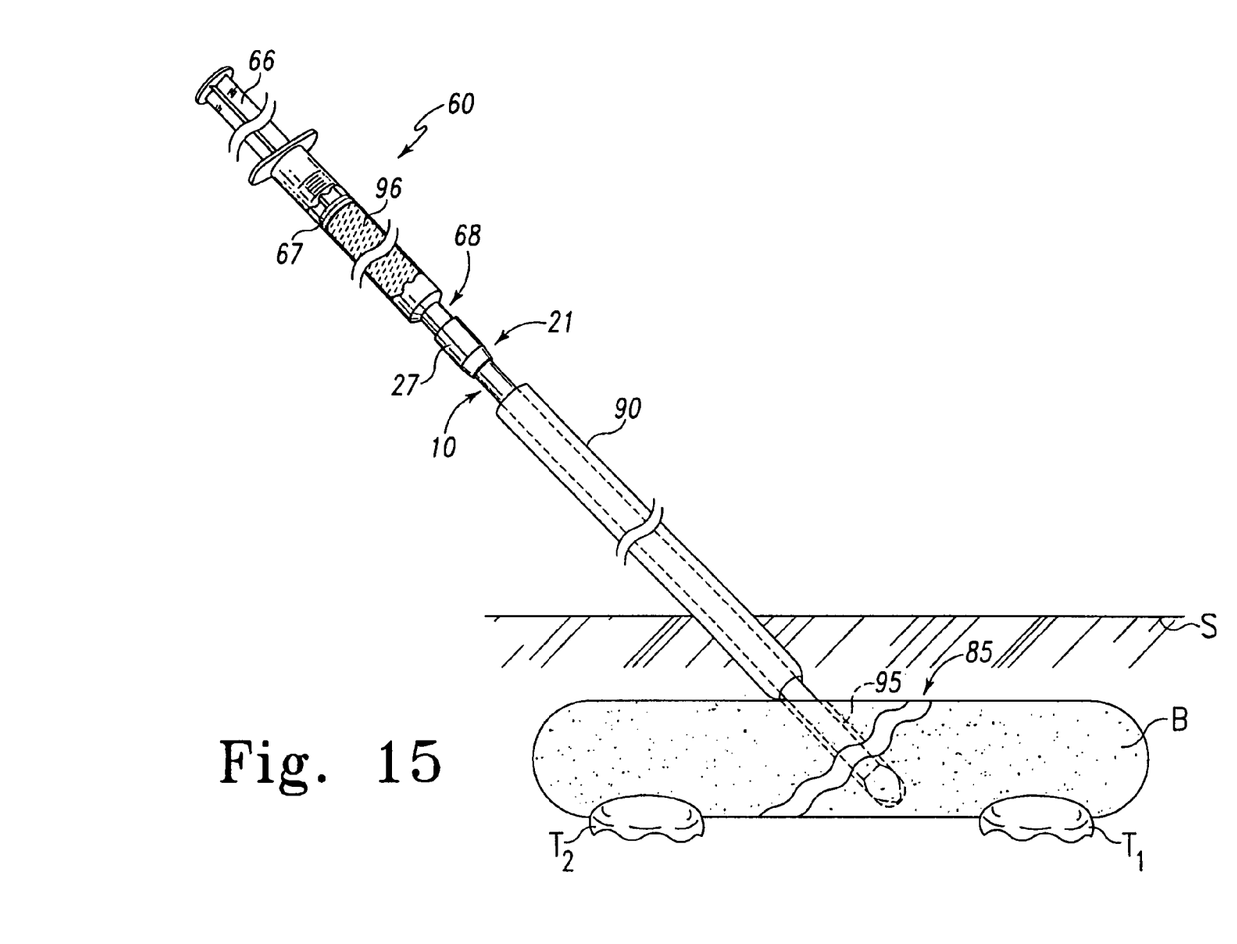
FIG. 15 is a side elevation view of the pseudoarthrotic mass of FIG. 14 depicting a syringe connected to the drill according to the present invention.

The drill, with obturator 30 disposed in its lumen, is then advanced so as to cut into the bone adjacent the pseudoarthrotic mass 85 as desired. At least one bore is drilled through the non-union, to the other side of the non-union as seen in FIG. 13. This procedure creates at least one channel 95 or other space for disposing the osteoinductive composition. At this point, K-wire 80 can be removed if desired. Obturator 30 can then be removed from lumen 25 of drill 10 as seen in FIG. 14 wherein K-wire 80 also has been removed. Distal end 62 of syringe 60 may then be matingly engaged, or otherwise fluidly connected, to proximal end 21 of drill 10 as seen in FIG. 15. Syringe 50 is advantageously filled with a desired amount of osteoinductive composition 96. The syringe 60 and drill 10 assembly can be used to deliver an osteogenic material to a pseudoarthrotic site.

Figure 16:
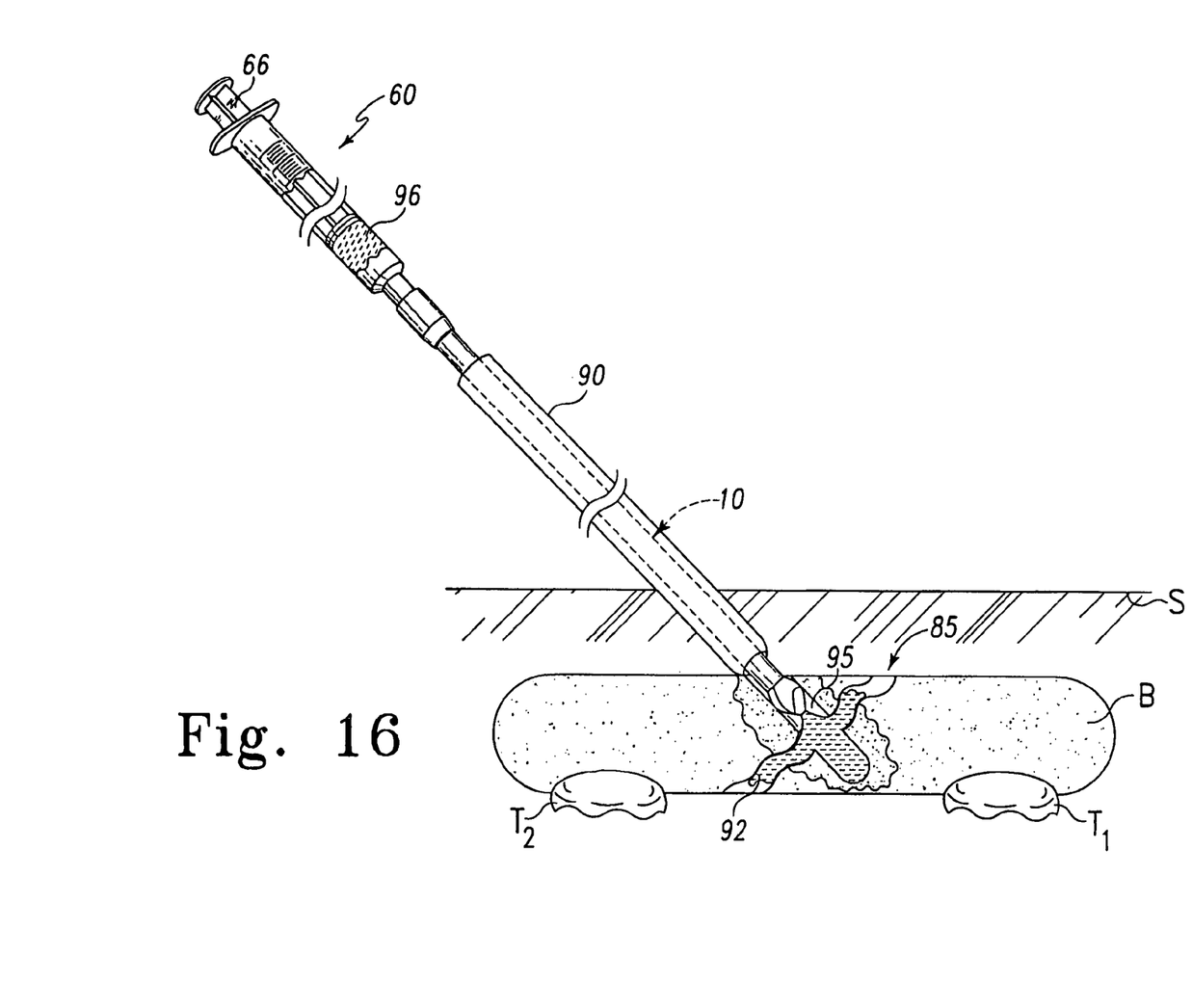
FIG. 16 is a side elevation view of the pseudoarthrotic site of FIG. 15 partially broken away and depicting delivery of an osteoinductive composition into a bored hole in the pseudoarthrotic mass according to the present invention.

Referring now to FIG. 16, drill 10 can be, but is not required to be, retracted, or otherwise-backed out of the channel, at the same time that plunger 66 is depressed so as to deliver osteoinductive composition 96 under pressure into the channel, or space, 95 and into at least a portion of the pseudoarthrotic mass 85. It should be understood that drill 10' or 10" can be used in the assemblies and methods described herein. When utilizing such a drill having apertures along a length of the drill, the osteoinductive material may be delivered to the fibrous tissue of the pseudoarthrotic mass 85 and may advantageously displace the fibrous tissue in or around the pseudoarthrotic site or be disposed throughout it. It is also realized that the osteoinductive composition may be injected under pressure with a syringe having a screw drive mechanism or ratcheting mechanism. In one embodiment, drill 10' or a delivery member 70 having apertures along a length of the drill or delivery member may be utilized to deliver osteoinductive material to a pseudoarthrotic site. The drill 10' or delivery number 70 can be positioned so that apertures 28 or 78 provided therein are adjacent to the pseudoarthrotic defect, channel 95 and/or spanning the entire pseudoarthrotic mass, or region, so that the osteoinductive material can be effectively deposited across the mass with minimal or no repositioning of the drill or delivery member. It is further noted when utilizing drill 10', should the apertures become restricted or otherwise clogged from cellular or other debris, the lumen of drill 10' may be perfused with a biocompatible solution, such as a biological saline solution, and the debris removed under pressure through the proximal end of drill 10'. Further, when utilizing an elongated member having apertures along a length of the member, that the guide wire may remain positioned in vivo during delivery of the osteogenic composition, so that the composition will be delivered primarily into the surrounding fibrous tissue.

Figure 17:
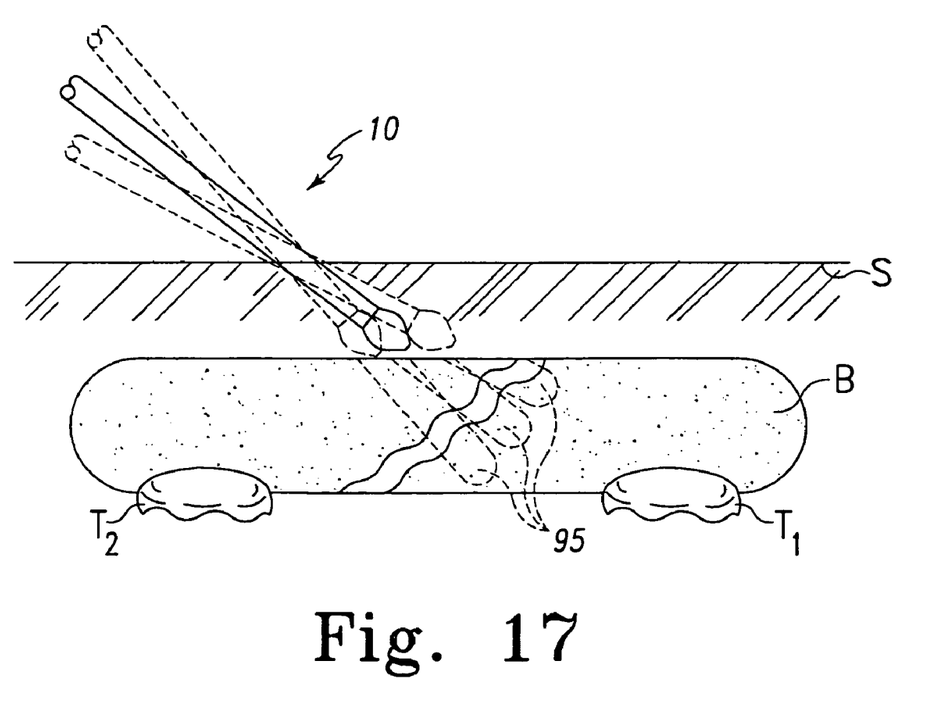
FIG. 17 is a side elevation view of the pseudoarthrotic mass of FIG. 11 depicting a plurality of holes bored into the mass according to one embodiment of the present invention.

Referring now to FIG. 17, in a alternative embodiment, any one of drill 10, 10' and 10" can be utilized to form channel 95. Drills 10 or 10' can be provided with or without connector 27, 27' for engagement with a syringe. After forming one or more bores or channels 95, drill 10, 10' or 10" can be partially or fully withdrawn from the treatment site. A syringe may then be connected on the proximal end of elongated delivery member 70 through which an osteoinductive composition cam be delivered.

In another aspect, while only a single incision, or other entry point, need be made in the skin and only a single injection of osteoinductive composition may be required, a plurality of channels 95 or other openings may be created by drill 10, 10' or 10". A plurality of channels 95 or other spaces can subsequently be filled with the osteoinductive composition as described herein. Alternately, a large incision may be made that fully exposes the pseudoarthritic site.

In performing the procedure to treat spinal pseudoarthrosis at an interbody fusion site, such as a lumbar or cervical fusion site, a similar procedures may be performed, further including holes, or other apertures, 99 into and optionally adjacent to the intervertebral spacer or fusion cage.

Figure 18:
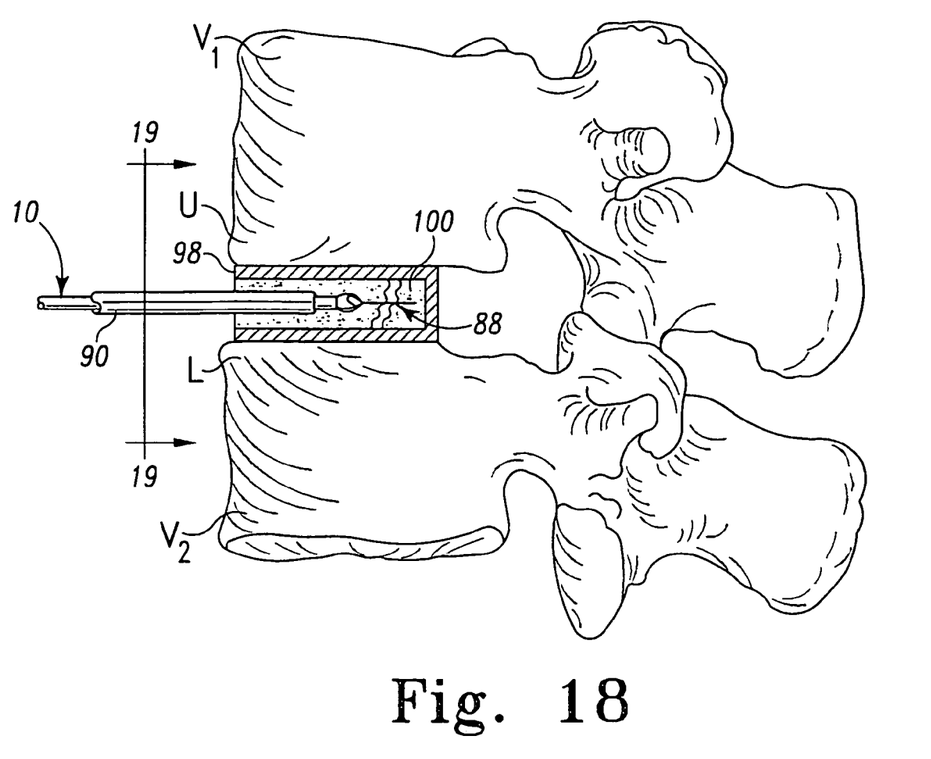
FIG. 18 is a side elevation view in partial section illustrating a fusion cage between a pair of vertebrae wherein a drill is positioned in a pseudoarthrotic mass located within a fusion cage according to another embodiment of the present invention.
Figure 19:
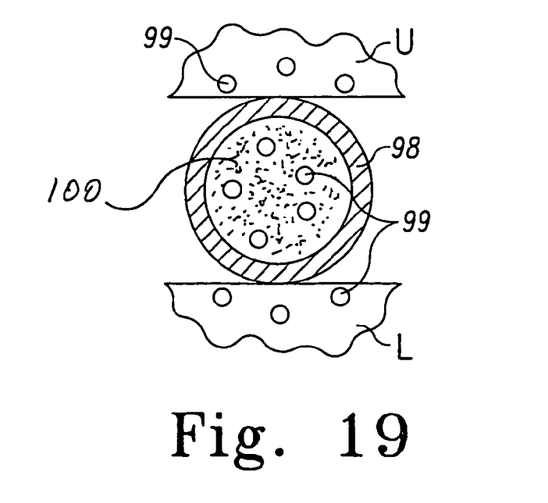
FIG. 19 is a cross-section view taken along line 19-19 of FIG. 18, illustrating a intervertebral implant, between adjacent vertebrae depicting a plurality of bore holes drilled in the pseudoarthrotic mass inside the implant chamber, as well as in the superior vertebral bodies, adjacent to the implant.

In another embodiment of treating pseudoarthrosis, referring to FIGS. 18 and 19, a pseudoarthrotic mass 100 is shown at a location within an intervertebral spacer 98. Drill 10 is operably positioned in and adjacent to a pseudoarthrotic mass in a fusion cage 98 to form channels or bores 99. In one embodiment cannulated drill 10 is disposed about a K-wire 88 in the lumen of cannula 90, positioned adjacent to the pseudoarthrotic mass 100. Bores or channels 99 are formed by drill 10 perforating pseudoarthrotic mass 100 and superior (upper) and inferior (lower) vertebral areas U and L, respectively, adjacent to the fusion cage 98.

It will be understood that while the present invention has been illustrated as a treatment of a pseudoarthrosis located at an intertransverse process fusion site, this invention can also be used to treat pseudoarthrosis in and about other bone tissue. For example, the load bearing bones or long bones of the limbs, can be advantageously treated according to the present invention. Pseudorthrisis of any of the different bone classes, i.e., long bones short bones, flat bones and irregular bones can be treated according to the present invention. Further all animals containing a skeletal structure including humans can be treated according to the present invention.

A osteoinductive composition for use in the invention may include an osteoinductive factor in a pharmaceutically acceptable carrier. A wide variety of osteoinductive factors can be used, including growth factors such as bone morphogenetic proteins (BMPs) and LIM mineralization proteins (LMPs) and Growth Differentiation Factors (GDFs). A wide variety of bone morphogenetic proteins are contemplated, including bone morphogenetic proteins designated as BMP-2 through BMP-18, including heterodimers thereof and combinations thereof. Other suitable growth factors include platelet-derived growth factors, insulin-like growth factors, epidermal growth factors, cartilage-derived morphogenic proteins, growth differentiation factors, such as growth differentiation factor 5; and transforming growth factors, including TGF-α and TGF-β, or other growth factors having osteoinductive properties. Proteins may include recombinant proteins, such as recombinant human proteins. Suitable recombinant human bone morphogenetic proteins (rhBMPs) include rhBMP-2 and rhBMP-7, but may also be derived from any other bone morphogenetic proteins described herein, heterodimers thereof and combinations thereof.

Bone morphogenic proteinds (BMPs) are available from Genetics Institute, Inc., Cambridge, Mass. and may also be prepared by one skilled in the art as described in U.S. Pat. Nos. 5,187,076 to Wozney et al.; 5,366,875 to Wozney et al.; 4,877,864 to Wang et al.; 5,108,922 to Wang et al.; 5,116,738 to Wang et al.; 5,013,649 to Wang et al.; 5,106,748 to Wozney et al.; and PCT Patent Nos. WO93/00432 to Wozney et al.; WO94/26893 to Celeste et al.; and WO94/26892 to Celeste et al. A wide variety of bone morphogenic proteins are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

The osteoinductive factors may be dispersed, or otherwise carried in, a wide variety of carriers. The carriers may be resorbable. Suitable carriers include aqueous buffers, collagen, gelatin, and synthetic resorbable polymers such as polylactic acid, polyglycolic acid, alternating copolymers of polylactic acid and polyglycolic acid, carboxymethylcellulose, mineral-containing materials, hyaluronic acid and other glycosaminoglycans, and combinations thereof. In certain forms of the invention, the carrier is a resorbable mineral-containing cement, such as a calcium phosphate cement.

Such calcium phosphate cements may be synthetic calcium phosphate materials that include a poorly or low crystalline calcium phosphate, such as a low or poorly crystalline apatite, including hydroxyapatite, available from Etex Corporation and as described, for example, in U.S. Pat. Nos. 5,783,217; 5,676,976; 5,683,461; and 5,650,176, and PCT International Publication Nos. WO 98/16268, WO 96/39202 and WO 98/16209, all to Lee et al. As defined in the recited patents and herein, the terms "poorly or low crystalline" calcium phosphate material refer to a material that is amorphous, having little or no long range order and/or a material that is nanocrystalline, exhibiting crystalline domains on the order of nanometers or Angstroms. The calcium: phosphate ratio of the carrier is typically in the range of about 0.3 to about 0.7, and in another embodiment is about 0.4 to about 0.6.

The osteoinductive compositions may include the osteoinductive factors, or nucleotide sequences that encode the respective osteoinductive factors so that the osteoinductive factor may be produced in vivo, in a pharmaceutically acceptable carrier. The nucleotide sequences therefore may be operably linked to a promoter sequence and may be inserted in a vector, including a plasmid vector and viral vectors. A nucleic acid sequence is "operably linked" to another nucleic acid sequence when it is placed in a specific functional relationship with the other nucleic acid sequence. Furthermore, predetermined cell-specific, inducible and constitutive promoters may be selected based on the operative environmental. In one embodiment, cells, including eukaryotic cells such as animal cells, may be transformed with nucleotide sequences encoding the osteoinductive factor and the osteoinductive composition will then include the transformed cells in a pharmaceutically acceptable carrier. In other forms, the osteoinductive composition includes a virus such as, for example, an adenovirus capable of eliciting intracellular production of a LIM mineralization protein.

A cell sustaining component can also be included in a resorbable cement carrier, a cell-sustaining component. The cell-sustaining component is one that provides nutrients to the cells so that they are able to produce the osteoinductive factor. The cell-sustaining component may be selected so that it does not substantially alter or otherwise modify the rate at which the carrier is resorbed. Such cell-sustaining components include collagen, and various cell culture media utilized for ex vivo cell culture, including an infusible media such as normal saline supplemented with about 5% human serum albumen (HSA), Dulbecco's Modified Eagle's medium (DMEM), or RPMI 1640 supplemented with fetal bovine serum or serum-free medium formulations such as the X VIVO products, or the components include a combination thereof. In yet other embodiments, the nucleotide sequences may be combined directly with the carrier for delivery.

The desired amount of osteoinductive factor included in the carrier, and the desired amount applied to the treatment site, is typically an amount effective in forming new bone to treat the spinal pseudoarthrosis. This amount will depend on a variety of factors, including the osteoinductive potential of the factor, the nature of the carrier, and the extent of pseudoarthrosis. In one embodiment, for example, the amount is in the range of about 0.5 mg BMP/ml carrier to about 4 mg BMP/ml carrier (corresponding to a weight ratio of BMP:dry carrier in the range of about 1:2000 to about 1:250). Further compositions embodiments may include about 1 mg BMP/ml carrier to about 3 mg BMP/ml carrier (corresponding to a weight ratio of BMP:dry carrier of about 1:1000 to about 1:333), while other embodiments include at least about 2 mg BMP/ml carrier (corresponding to a weight ratio of BMP:dry carrier of at least about 1:500). The amount of the osteoinductive composition applied to the fusion site will also vary due to factors as described above. For example, the amount in one embodiment is sufficient to deliver about 2 mg BMP to about 40 mg BMP, about 4 mg BMP to about 20 mg BMP in another embodiment and at least about 12 mg BMP in yet another embodiment.

The procedure may be performed at interbody fusion sites involving a wide variety of implants, such as those having a chamber therein that is open towards an anterior or posterior site. Such implants include those found in U.S. Pat. Nos. 4,961,740; 5,015,247 and 5,423,817, wherein an end cap is not used to close the chamber of these implants from access by an anterior or posterior approach. The procedure herein may be performed at sites including implants with end caps after penetration or removal of the end cap.

While embodiments of the invention have been illustrated and described in detail in the drawings and foregoing description, the same is to be considered as illustrative and not restrictive in character, it being understood that all changes and modifications that come within the spirit of the invention are desired to be protected. In addition, all references cited herein are hereby incorporated by reference in their entirety.

What is claimed is:

1. A cannulated drill, comprising an elongated member formed of a biocompatible material and having a proximal end, a distal end, an inner cylindrical surface, and an outer surface, said inner cylindrical surface defining a cylindrical lumen having an inner diameter, said cylindrical lumen extending along the length of said elongated member and sized to receive an elongated obturator, said elongated member having a distal cutting portion including a plurality of bone cutting edges extending about and along said distal cutting portion, said cylindrical lumen extending through said distal cutting portion and defining a distal opening at a distal end surface of said distal cutting portion, said elongated member having a connector adjacent said proximal end configured for matingly engaging a distal end portion of a syringe, and further comprising an elongated obturator, said obturator having an outer cylindrical surface defining an outer diameter conforming to said inner diameter of said cylindrical lumen to permit said obturator to be slidably disposed in said cylindrical lumen and wherein a distal-most end of said obturator is positioned at said distal opening to inhibit material from entering said distal opening and into said cylindrical lumen; and wherein said obturator defines a longitudinal passage that extends from a proximal end of said obturator to said distal end of said obturator; and further comprising an elongate guide member positioned within said longitudinal passage in said obturator to guide the drill as the drill is axially advanced along said elongate guide member, and a cannula defining an axial lumen extending therethrough from a proximal end to a distal end; and wherein said elongated member is positioned within said axial lumen with said distal cutting portion positioned beyond said distal end of said cannula.

2. The drill of claim 1, wherein said outer surface of said elongated member is cylindrical.

3. The drill of claim 1, wherein said elongated member is formed of a biocompatible metallic material.

4. The drill of claim 1, wherein said distal end of said obturator is blunt.

5. The drill of claim 1, wherein said elongated member has a cylindrical shaft that includes said proximal end and a head that includes said distal end, said head having a width larger than the width of said shaft.

6. The drill of claim 1, further comprising:

a syringe having a housing defining a cavity, said syringe matingly engaged to said elongated member by said connector, said lumen of said elongated member and said cavity of said housing in fluid communication when said syringe is matingly engaged to said elongated member; and an osteoinductive composition including a bone growth factor positioned in said cavity of said syringe for delivery into said lumen of said elongated member upon actuation of said syringe.

7. The drill of claim 6, wherein said osteoinductive composition comprises a bone morphogenic protein.

8. The drill of claim 1, wherein said elongate guide member has a pointed distal end configured to pierce into bone.

9. The drill of claim 1, wherein said elongate guide member comprises a K-wire.

10. The drill of claim 1, wherein said inner diameter of said cylindrical lumen is uniform from said distal opening to said proximal end.

11. The drill of claim 1, wherein said cutting edges comprise helical cutting edges that extend helically about and along said distal cutting portion.

12. The drill of claim 1, wherein said distal end of said cannula includes a rounded distal end surface.

13. A cannulated drill, comprising an elongated member formed of a biocompatible material and having a proximal end, a distal end, an inner surface, and an outer surface, said inner surface defining a cylindrical lumen, said cylindrical lumen extending along the length of said elongated member and sized to receive an elongated obturator, said distal end of said elongated member having a distal cutting portion including a plurality of cutting edges extending about and along said distal cutting portion, said cylindrical lumen extending through said distal cutting portion and defining a distal opening at a distal end surface of said distal cutting portion, said proximal end of said elongated member having a connector configured for matingly engaging a distal end of a syringe to said proximal end of said elongated member, and further comprising an elongated obturator, said obturator slidably disposed in said cylindrical lumen and wherein a distal-most end of said obturator is positioned at said distal opening of said distal cutting portion to inhibit material from entering said distal opening and into said cylindrical lumen, said obturator having a longitudinal passage extending through the entirety of said obturator; and an elongate guide member positioned within said longitudinal passage in said obturator to guide the drill as the drill is axially advanced along said elongate guide member; and a cannula defining an axial lumen extending therethrough from a proximal end to a distal end; and wherein said elongated member is positioned within said axial lumen with said distal cutting portion positioned beyond said distal end of said cannula.

14. The drill of claim 13, wherein said cutting edges of said distal cutting portion intersect said distal opening.

15. The drill of claim 13, wherein said distal cutting portion has a bulbous shape having a first proximal diameter, a second medial diameter that is larger than said first diameter, and a distalmost part having a diameter smaller than said second diameter.

16. The drill of claim 15, wherein said bulbous shape has a rounded configuration.

17. The drill of claim 13, further comprising:

a syringe having a housing defining a cavity, said syringe matingly engaged to said elongated member by said connector, said lumen of said elongated member and said cavity of said housing in fluid communication when said syringe is matingly engaged to said elongated member; and an osteoinductive composition including a bone growth factor positioned in said cavity of said syringe for delivery into said lumen of said elongated member upon actuation of said syringe.

18. The drill of claim 13, wherein said elongate guide member has a pointed distal end configured to pierce into bone.

19. The drill of claim 13, wherein said elongate guide member comprises a K-wire.

20. The drill of claim 13, wherein said cylindrical lumen has an inner diameter that is uniform from said distal opening to said proximal end.

21. The drill of claim 13, wherein said cutting edges comprise helical cutting edges that extend helically about and along said distal cutting portion.

22. The drill of claim 13, wherein said distal end of said cannula includes a rounded distal end surface.

23. A cannulated drill, comprising an elongated member formed of a biocompatible material and having a proximal end, a distal end, an inner surface, and an outer surface, said inner surface defining a cylindrical lumen, said cylindrical lumen extending along the length of said elongated member and sized to receive an elongated obturator, said distal end of said elongated member having a distal cutting portion including a plurality of cutting edges extending about and along said distal cutting portion, said cylindrical lumen extending through said distal cutting portion and defining a distal opening at a distal end surface of said distal cutting portion, said proximal end of said elongated member having a connector configured for matingly engaging a distal end of a syringe to said proximal end of said elongated member, and further comprising an elongated obturator, said obturator slidably disposed in said cylindrical lumen, wherein said elongated member has a plurality of apertures extending along its length in communication with said cylindrical lumen, and said obturator has a forwardmost position within said cylindrical lumen at which all of said apertures are blocked by said obturator and wherein a distal-most end of said obturator is positioned at said distal opening of said distal cutting portion to inhibit material from entering said distal opening and into said cylindrical lumen when in said forwardmost position, and withdrawing said obturator from said forwardmost position unblocks said apertures and said distal opening; and wherein said obturator defines a longitudinal passage along its entire length; and further comprising an elongate guide member positioned within said longitudinal passage in said obturator to guide the drill as the drill is axially advanced along said elongate guide member, and a cannula defining an axial lumen extending therethrough from a proximal end to a distal end; and wherein said elongated member is positioned within said axial lumen with said distal cutting portion positioned beyond said distal end of said cannula.

24. The drill of claim 23, wherein said plurality of apertures include a first set and a second set, said first set of apertures being diametrically opposed to said second set of apertures.

25. The drill of claim 23, further comprising:

a syringe having a housing defining a cavity, said syringe matingly engaged to said elongated member by said connector, said lumen of said elongated member and said cavity of said housing in fluid communication when said syringe is matingly engaged to said elongated member; and an osteoinductive composition including a bone growth factor positioned in said cavity of said syringe for delivery into said lumen of said elongated member upon actuation of said syringe.

26. The drill of claim 23, wherein said elongate guide member has a pointed distal end configured to pierce into bone.

27. The drill of claim 23, wherein said elongate guide member comprises a K-wire.

28. The drill of claim 23, wherein said cylindrical lumen has an inner diameter that is uniform from said distal opening to said proximal end.

29. The drill of claim 23, wherein said cutting edges comprise helical cutting edges that extend helically about and along said distal cutting portion.

30. The drill of claim 23, wherein said distal end of said cannula includes a rounded distal end surface.

* * * * *